United States Patent

Annen et al.

[11] Patent Number: 4,645,763
[45] Date of Patent: * Feb. 24, 1987

[54] 6α-METHYL CORTICOIDS, THEIR PRODUCTION AND USE

[75] Inventors: Klaus Annen; Henry Laurent; Helmut Hofmeister; Rudolf Wiechert; Hans Wendt, all of Berlin, Fed. Rep. of Germany

[73] Assignee: Schering Aktiengesellschaft, Berlin and Bergkamen, Fed. Rep. of Germany

[*] Notice: The portion of the term of this patent subsequent to Nov. 26, 2002 has been disclaimed.

[21] Appl. No.: 554,418

[22] Filed: Nov. 22, 1983

[30] Foreign Application Priority Data

Nov. 22, 1982 [DE] Fed. Rep. of Germany ....... 3243482

[51] Int. Cl.⁴ ............................................... A61K 31/56
[52] U.S. Cl. ............................. 514/178; 260/397.45; 260/239.55 D; 514/170
[58] Field of Search .................................... 260/397.45

[56] References Cited
U.S. PATENT DOCUMENTS 4,243,664 1/1981 Annen et al. .................... 260/397.45

OTHER PUBLICATIONS

Sugai et al., "Synthesis", 1982 (12) pp. 1023–1025, as abstracted in Chem. Abstr., vol. 98, Par. 143712t.

Primary Examiner—Elbert L. Roberts
Attorney, Agent, or Firm—Millen & White

[57] ABSTRACT

6α-Methyl corticoids of formula I

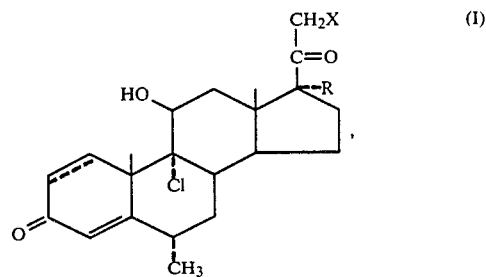

wherein ⋯ is a single bond or a double bond, R is acyloxy of up to 8 carbon atoms, and X is chlorine, hydroxy, or acyloxy of up to 8 carbon atoms, are pharamacologically effective substances.

16 Claims, No Drawings

6α-METHYL CORTICOIDS, THEIR PRODUCTION AND USE

This invention relates to new steroids having valuable pharmacological properties.

SUMMARY OF THE INVENTION

It is an object of this invention to provide such new compounds.

These objects have been achieved by providing 6α-methyl corticoids of formula I

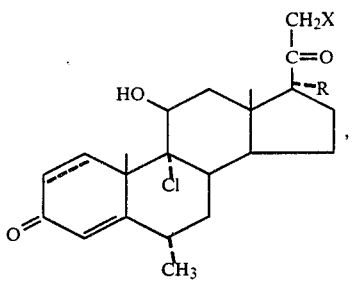

wherein ⸺ is a single or double bond, R is an acyloxy group of up to 8 carbon atoms, and X is chlorine, hydroxy or an acyloxy group of up to 8 carbon atoms.

DETAILED DISCUSSION

The new 6α-methyl corticoids of formula I can carry as acyloxy groups R and X, $C_{1-8}$ aliphatic, $C_{3-8}$ cycloaliphatic or Chd 6–10 aromatic radicals, e.g., acetoxy, propionyloxy, butyryloxy, isobutyryloxy, valeryloxy, 3-methylbutyryloxy, trimethylacetoxy, hexanoyloxy, benzoyloxy, etc. Herein, alkanoyloxy includes cycloalkanoyloxy, for example.

It has been found that the 6α-methyl corticoids of this invention surprisingly often have a markedly stronger anti-inflammatory effect upon topical application than the previously known 6α-methyl corticoids. This effectiveness is often even significantly stronger than that of difluorinated "noble corticoids" like the 6α,9α-difluoro-11β-hydroxy-16α-methyl-21-valeryloxy-1,4-pregnadiene-3,20-dione (=Nerisona). Upon systemic application, the 6α-methyl corticoids of this invention are surprisingly often less effective anti-inflammatorily than the corresponding previously known 6α-methyl corticoids. In all cases, the compounds have at least good topical anti-inflammatory activity. When this is accompanied by low systemic activity, the combination is very advantageous.

The new 6α-methyl corticoids of this invention accordingly are suited, in combination with the usual excipients used in galenic pharmacy, for the local treatment in mammals, including humans, of contact dermatitis, all kinds of eczema, neurodermatoses, erythrodermia, burns, pruritis vulvae et ani, rosacea, erythematodes cutaneus, psoriasis, lichen ruber planus et verrucosus and similar skin diseases.

The production of the pharmaceutical specialties is carried out in the usual way, that is, the active ingredients together with suitable additives are transformed into the desired form of application, e.g., solutions, lotions, salves, creams or plasters. In the pharmaceuticals so formulated, the concentration of the active ingredient is dependent on the form of application. In lotions and salves a concentration of 0.001 to 1 percent is preferred. Administration is as conventional with such topical formulations, e.g., as with a hydrocortisone cream.

Moreover, the new compounds, optionally in combination with the usual excipients and adjuvants, are also well suited for the production of inhalants, which can be used for treating allergic illnesses of the breathing passages, such as bronchial asthma or rhinitis. These can be administered analogously to the conventional inhalant beclomethasone dipropionate.

In addition, the new corticoids are suitable in view of their systemic activity, for use in the form of capsules, tablets, or dragees, which preferably contain 10–200 mg of active ingredient and are administered orally (e.g., at a daily dosage of 0.2–20 mg/kb), or in the form of suspensions, which preferably contain 100–500 mg of active ingredient per dose unit and are administered rectally (at the same daily dosage). They can also be used to treat allergic illnesses of the intestinal tract such as colitis ulcerosa and colitis granulomatosa, analogously to the administration of the conventional betamethasone disodium phosphate.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohol, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For enternal application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol.

The new 6α-methyl corticoids can be produced using known processes carried out under conditions, e.g., as described in German patent applications Nos. 26 45 104, 26 45 105, 23 40 591, and 19 58 549; in U.S. Pat. No. 3,383,394; and in the J. Org. Chem 38, 1973, 4203, all of whose disclosures are incorporated by reference herein. For example, such reactions include: a process for producing a 6α-methyl corticoid of formula Ia:

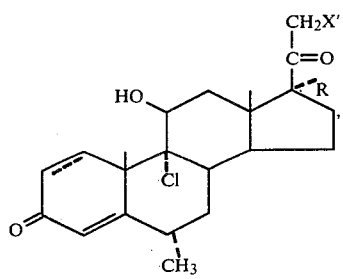

(Ia)

wherein •⋯• is a single bond or a double bond, R is acyloxy of a maximum of 8 carbon atoms, and X' is chlorine or acyloxy of a maximum of 8 carbon atoms, which comprises conventionally (a) esterifying or chlorinating in the 21-position, a 6α-methyl corticoid of formula II

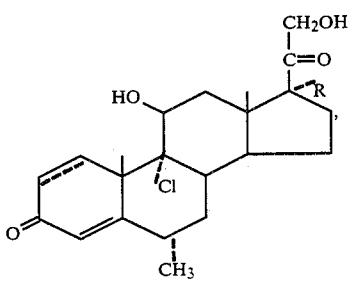

(II)

wherein •⋯• and R are defined as above;

(b) treating a 6α-methyl corticoid of formula III

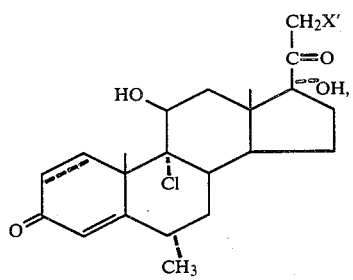

(III)

wherein •⋯• X' and R are defined as above, to etherify it in the 11-position with a trialkylsilyl compound or esterify it in the 11-position with a derivative of a strongly acidic monocarboxylic acid, subsequently acylating the 17-position with a carboxylic acid chloride or carboxylic acid anhydride corresponding to the R group in the presence of 4-dimethylaminopyridine, and then splitting off the blocking group in the 11-position; or (c) adding hypochlorous acid to the $\Delta^{8(11)}$ double bond of a 6α-methyl corticoid of formula IV

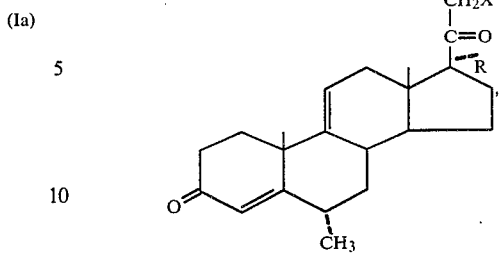

(IV)

wherein •⋯• X' and R are as defined above; and a process for producing 6α-methyl corticoids of formula (Ib)

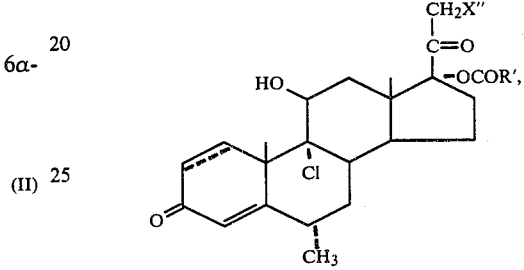

(Ib)

wherein •⋯• is a single bond or a double bond and R' is an alkyl or cycloalkyl group with a maximum of 7 carbon atoms or a phenyl group or other appropriate hydrocarbon moiety of an anacyloxy group, and X" is hydroxy or chlorine, which comprises, in a way known to men of skill in the art, splitting hydrolytically or with trimethylchlorosilane, the ortho ester group or a corticoid of formula V

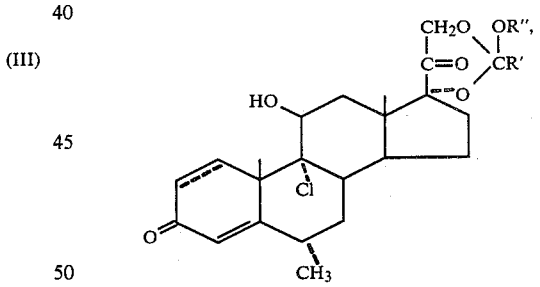

(V)

wherein •⋯• and R' are as defined above and R" is an alkyl radical of 1-4 carbon atoms.

All starting materials required in these reactions are known or readily preparable using conventional methods.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) 150 ml benzene are distilled off at 130° C. by a water separator from a solution of 5.0 g of 9α-chloro-11β,17α,21-trihydroxy-6α-methyl-1,4-pregnadiene-3,20-dione and 0.5 g of pyridinium tosylate in 35 ml of dimethylformamide and 350 ml of benzene. 10 ml of orthoacetic acid triethyl ester are fed slowly into the hot reaction solution, and then more benzene and readily volatile reaction components are distilled off. Then 4 ml of pyridine are added, and concentrated to dryness under vacuum. 9α-chloro-17α,21-(ethoxyethylidenedioxy)-11β-hydroxy-6α-methyl-1,4-pregnadiene-3,20-dione is isolated as an oil.

(b) The raw 9α-chloro-17α,21-(ethoxyethylidenedioxy)-11β-hydroxy-6α-methyl-1,4-pregnadiene-3,20-dione is dissolved in 150 ml of ethanol and stirred with a mixture of 54 ml of 0.1N acetic acid and 6 ml of 0.1 M aqueous sodium acetate solution for 1 hour in a 100° C. bath temperature. The solution is then concentrated to ⅓ the volume and added to water. The ethyl acetate extracts are washed neutral. After drying and concentration, the raw product is purified on 500 g of silica gel with a methylene chloride-acetone gradient (0–20% acetone). 4.6 g of 17-α-acetoxy-9α-chloro-11β,21-dihydroxy-6α-methyl-1,4-pregnadiene-3,20-dione, with a melting point of 216°–218° C., are obtained.

EXAMPLE 2

(a) Analogously to example 1(a), 2.0 g of 9α-chloro-11β,17α,21-trihydroxy-6α-methyl-1,4-pregnadiene-3,20-dione are reacted with orthopropionic acid triethyl ester to form 9α-chloro-17α,21-(ethoxypropylidenedioxy)-11β-hydroxy-6α-methyl-1,4-pregnadiene-3,20-dione as an oil.

(b) The raw 9α-chloro-17α,21-(ethoxypropylidenedioxy)-11β-hydroxy-6α-methyl-1,4-pregnadiene-3,20-dione is reacted as in example 1(b), processed and purified. 1.6 g of 9α-chloro-11β,21-dihydroxy-6α-methyl-17α-propionyloxy-1,4-pregnadiene-3,20-dione, with a melting point of 201°–203° C., are isolated.

EXAMPLE 3

(a) 8 ml of methane sulfonic acid chloride are added drop by drop to a solution of 12.8 g of 21-acetoxy-11β-hydroxy-6α-methyl-17α-propionyloxy-1,4-pregnadiene-3,20-dione in 65 ml of dimethyl formamide and 15 ml of pyridine at room temperature and then stirred for 2 hours more at a bath temperature of 80° C. After ice water precipitation and the usual processing, the raw product is purified on 800 g of silica gel with a methylene chloride-acetone gradient (0–8% acetone). 7.0 g of 21-acetoxy-6α-methyl-17α-propionyloxy-1,4,9(11)-pregnatriene-3,20-dione, with a melting point of 185°–187° C., are obtained.

(b) 2.0 g of 21-acetoxy-6α-methyl-17α-propionyloxy-1,4,9(11)-pregnatriene-3,20-dione are dissolved in 20 ml of dioxane and mixed with 1.8 g of N-chlorosuccinimide. 10 ml of a 10% perchloric acid solution are added drop by drop, and the mixture is stirred 5 at room temperature. After ice water precipitation and the usual processing, the raw product is purified on 200 g of silica gel with a methylene chloride-acetone gradient (0–12% acetone). The yield is 1.6 g of 21-acetoxy-9α-chloro-11β-hydroxy-6α-methyl-17α-propionyloxy-1,4-pregnadiene-3,20-dione, with a melting point of 232°-233° C.

EXAMPLE 4

(a) A solution of 2.7 g of tristriphenylphosphine-rhodium-I-chloride in 75 ml of methanol and 225 ml of benzene is prehydrogenated for 1 hour at room temperature. After the addition of 3.0 g of 21-acetoxy-6α-methyl-17α-propionyloxy-1,4,9(11)-pregnatriene-3,20-dione, the solution is further hydrogenated for 6.5 hours. After concentration to dryness, the residue is purifid on 350 g of silica gel with a hexane-ethyl acetate gradient (0–40% ethyl acetate). The yield is 2.5 g of 21-acetoxy-6α-methyl-17α-propionyloxy-4,9(11)-pregnadiene-3,20-dione, with a melting point of 149°–151° C.

(b) Under the conditions of example 3(b), 2.0 g of 21-acetoxy-6α-methyl-17α-propionyloxy-4,9(11)-pregnadiene-3,20-dione are reacted with N-chlorosuccinimide, processed and purified. 1.05 g of 21-acetoxy-9α-chloro-11β-hydroxy-6α-methyl-17α-propionyloxy-4-pregnene-3,20-dione, with a melting point of 205°–206° C. are isolated.

EXAMPLE 5

(a) Analogously to example 1(a), 5.0 g of 17α,21-dihydroxy-6α-methyl-1,4,9(11)-pregnatriene-3,20-dione are reacted with 10 ml of orthopropionic acid triethyl ester to form 17α,21-(ethoxypropylidenedioxy)-6α-methyl-1,4,9(11)-pregnatriene-3,20-dione oil as an oil.

(b) The raw 17α,21-(ethoxypropylidenedioxy)-6α-methyl-1,4,9(11)-pregnatriene-3,20-dione is stirred in 250 ml of dimethylformamide and 5 ml of trimethylchlorosilane for 20 hours at a bath temperature of 80° C. After concentration to drynees, the raw product is purified on 600 g of silica gel with a methylene chloride-acetone gradient (0–12% acetone). The yield is 3.5 g of 21-chloro-6α-methyl-17α-propionyloxy-1,4,9(11)-pregnatriene-3,20-dione.

(c) Analogously to example 3(b), 1.5 g of 21-chloro-6α-methyl-17α-propionyloxy-1,4,9(11)-pregnatriene-3,20-dione are reacted with N-chlorosuccinimide, processed and purified. 1.32 g of 9α,21-dichloro-11β-hydroxy-6α-methyl-17α-propionyloxy-1,4-pregnadiene-3,20-dione, with a melting point of 239°-241° C. are isolated.

EXAMPLE 6

(a) Analogously to example 1(a), b 2.0 g of 17α,21-dihydroxy-6α-methyl-1,4,9(11)-pregnatriene-3,20-dione are reacted with orthobutyric acid triethyl ester to form 17α,21-(ethoxybutylidenedioxy)-6α-methyl-1,4,9(11)-pregnatriene-3,20-dione as an oil.

(b) The raw 17α,21-(ethoxybutylidenedioxy)6α-methyl-1,4,9(11)-pregnatriene-3,20-dione, under the conditions in example 1(b), is treated with a mixture of 0.1N acetic acid and 0.1 M sodium acetate solutions, processed and purified. 1.5 g of 17α-butyryloxy-21-hydroxy-6α-methyl-1,4,9(11)-pregnatriene-3,20-dione are obtained.

(c) A solution of 1.0 g of 17α-butyryloxy-21-hydroxy-6α-methyl-1,4,9(11)-pregnatriene-3,20-dione in 10 ml of pyridine is stirred with 5.0 ml of acetic acid anhydride for 1 hour at room temperature and then processed as usual. After recrystallization from acetone/hexane, 930 mg of 21-acetoxy-17α-butyryloxy-6α-methyl-1,4,9(11)-pregnatriene-3,20-dione are isolated.

(d) Under the conditions of example 3(b), 800 mg of 21-acetoy-17α-butyryloxy-6α-methyl-1,4,9(11)-pregnatriene-3,20-dione are reacted with N-chlorosuccinimide, processed and purified. The yield is 650 mg of 21-acetoxy-17α-butyryloxy-9α-chloro-11β-hydroxy-6α-methyl-1,4-pregnadiene-3,20-dione, with a melting point of 227°–229° C.

EXAMPLE 7

(a) 60 ml of a 1.6 M lithium methyl solution are added drop by drop at 0° C. under argon to a suspension of 12.2 g of copper(I) iodide in 240 ml of anhydrous tetrahydrofuran. The solution is stirred 15 minutes at 0° C. and the yellow solution is cooled to −30° C. After addition, drop by drop, of a solution of 9.6 g of 17α-hydroxy-6α-methyl-21-valeryloxy-1,4,9(11)-pregnatriene-3,20-dione, the reaction mixture is stirred again 40 minutes at −30° C., then added to an ice-cold saturated ammonium chloride solution and extracted with ethyl acetate. The organic extracts are processed as usual, and the raw product is purified on 100 g of silica gel with a methylene chloride-acetone gradient (0–12% acetone). The yield is 7.3 g of 21-hydroxy-6α-methyl-17α-valeryloxy-1,4,9(11)-pregnatriene-3,20-dione.

(b) As in example 6(c), 5.0 g of 21-hydroxy-6α-methyl-17α-valeryloxy-1,4,9(11)-pregnatriene-3,20-dione are reacted with propionic acid anhydride, processed and purified. 4.6 g of 6α-methyl-21-propionyloxy-17α-valeryloxy-1,4,9(11)-pregnatriene-3,20-dione are isolated.

(c) Under the conditions of example 3(b), 4.0 g of 6α-methyl-21-propionyloxy-17α-valeryloxy-1,4,9(11)-pregnatriene-3,20-dione are reacted with N-chlorosuccinimide, processed and purified. The yield is 2.9 g of 9α-chloro-11β-hydroxy-6α-methyl-21-propionyloxy-17α-valeryloxy-1,4-pregnadiene-3,20-dione, with a melting point of 257°–259° C.

EXAMPLE 8

(a) As in example 1(a), 5.0 g of 17α,21-dihydroxy-6α-methyl-1,4,9(11)-pregnatriene-3,20-dione are reacted with 10 ml of orthobenzoic acid triethyl ester to form 17α,21-(ethoxybenzylidenedioxy)-6α-methyl-1,4,9(11)-pregnatriene-3,20-dione and processed.

(b) The raw 17α,21-(ethoxybenzylideneoxy)-6α-methyl-1,4,9(11)-pregnatriene-3,20-dione is reacted under the conditions of example 5(b), with trimethylchlorosilane, processed and purified. 3.2 g of 17α-benzoyloxy-21-chloro-6α-methyl-1,4,9(11)-pregnatriene-3,20-dione are isolated.

(c) Analogously to example 3(b), 1.0 g of 17α-benzoyloxy-21-chloro-6α-methyl-1,4,9(11)-pregnatriene-3,20-dione is reacted with N-chlorosuccinimide, processed and purified. The yield is 920 mg of 17α-benzoyloxy-9α,21-dichloro-11β-hydroxy-6α-methyl-1,4-pregnadiene-3,20-dione, with a melting point of 230°–232° C.

EXAMPLE 9

(a) A solution of 6.5 g of 21-acetoxy-17α-hydroxy-6α-methyl-1,4,9(11)-pregnatriene-3,20-dione in 80 ml of diethyl glycol dimethyl ether is stirred with 20.0 g of 4-dimethylaminopyridine and 20.0 ml of pivalic acid anhydride 5d at a bath temperature of 80° C. After ice water precipitation and the usual processing, the raw products is purified on 750 g of silica gel with a methylene chloride-acetone gradient (0–8 percent acetone). 4.6 g of 21-acetoxy-6α-methyl-17α-trimethylacetoxy-1,4,9(11)-pregnatriene-3,20-dione, with a melting point of 238°–240° C. are isolated.

(b) Under the conditions of example 3(b), 2.0 g of 21-acetoxy-6α-methyl-17α-trimethylacetoxy-1,4,9(11)-pregnatriene-3,20-dione are reacted with N-chlorosuccinimide, processed and purified. The yield is 1.56 g of 21-acetoxy-9α-chloro-11β-hydroxy6α-methyl-17α-trimethylacetoxy-1,4-pregnatriene-3,20-dione, with a melting point of 264–265° C.

EXAMPLE 10

(a) 1.8 g of tristriphenylphosphine-rhodium-I-chloride are prehydrogenated in 50 ml of MeOH and 150 ml of tetrahydrofuran for 1 hour. After addition of 2.0 g of 21-acetoxy-6α-methyl-17α-trimethylacetoxy-1,4,9(11)-pregnatriene-3,20-dione, hydrogenation continues for 5.5 hours, followed by concentration to dryness. The residue is purified on 300 g of silica gel with a hexane-ethyl acetate gradient (0–50 percent ethyl acetate). 1.5 g of 21-acetoxy-6α-methyl-17α-trimethylacetoxy-4,9(11)-pregnadiene-3,20-dione, with a melting point of 162°–163° C. are isolated.

(b) 1.3 g of 21-acetoxy-6α-methyl-17α-trimethylacetoxy-4,9(11)-pregnadiene-3,20-dione, under the conditions of example 3(b), are reacted, processed and purified. The yield is 560 mg of 21-acetoxy-9α-chloro-11β-hydroxy-6α-methyl-17α-trimethylacetoxy-4-pregnene-3,20-dione, with a melting point of 235°–237° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 6α-methyl corticoid of the formula

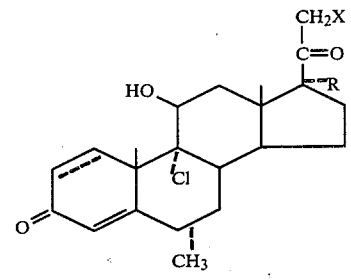

wherein ⋯ is a single bond, R is $C_{1-8}$-alkanoyloxy or benzoyloxy and X is chlorine, hydroxy, $C_{1-8}$-alkanoyloxy or benzoyloxy.

2. A compound of claim 1, wherein R is acetoxy, propionyloxy, benzoyloxy, valeryloxy, trimethylacetoxy, or butyryloxy.

3. A compound of claim 1, wherein X is OH, acetoxy, Cl, or propionyloxy.

4. 21-acetoxy-9α-chloro-11β-hydroxy-6α-methyl-17α-propionyloxy-4-pregnene-3,20-dione, a compound of claim 1.

5. 21-acetoxy-9α-chloro-11β-hydroxy-6α-methyl-17α-trimethylacetoxy-4-pregnene-3,20-dione, a compound of claim 1.

6. A pharmaceutical composition comprising an antiinflammatorily effective amount of a compound of claim 1 and a pharmaceutically acceptable carrier.

7. A pharmaceutical composition of claim 6 which is adpated for topical administration.

8. A pharmaceutical composition of claim 6, comprising two of said anti-inflammatory compounds.

9. A method of achieving an anti-inflammatory effect in a patient in need of such treatment comprising administering to the patient an effective amount of a compound of claim 1.

10. A 6α-methyl corticoid of the formula

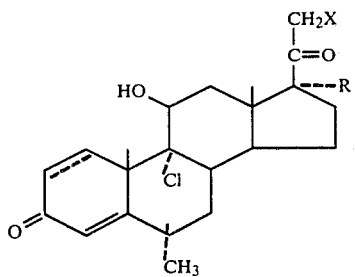

wherein $\cdots$ is a single or double bond, R is $C_{1-8}$-alkanoyloxy or benzoyloxy and X is chlorine.

11. 9α,21-dichloro-11β-hydroxy-6α-methyl-17α-propionyloxy-1,4-pregnadiene-3,20-dione, a compound of claim 10.

12. 17α-benzoyloxy-9α,21-dichloro-11β-hydroxy-6α-methyl-1,4-pregnadiene-3,20-dione, a compound of claim 10.

13. A pharmaceutical composition comprising an anti-inflammatorily effective amount of a compound of claim 10 and a pharmaceutically acceptable carrier.

14. A pharmaceutical composition of claim 13 which is adapted for topical administration.

15. A pharmaceutical composition of claim 13 comprising two of said anti-inflammatory compounds.

16. A method of achieving an anti-inflammatory effect in a patient in need of such treatment comprising administering to the patient an effective amount of a compound of claim 10.

* * * * *